United States Patent [19]

Thiem et al.

[11] Patent Number: 4,552,981

[45] Date of Patent: Nov. 12, 1985

[54] PROCESS FOR THE PRODUCTION OF 5-NITRO-ACET-2,4-XYLIDINE

[75] Inventors: Karl W. Thiem, Charleston; Daniel P. Vanderpool, Hanahan, both of S.C.

[73] Assignee: Mobay Chemical Corporation, Pittsburgh, Pa.

[21] Appl. No.: 325,540

[22] Filed: Nov. 27, 1981

[51] Int. Cl.$^4$ ............................................. C07C 102/00
[52] U.S. Cl. ..................................... 564/146; 564/166; 564/218; 564/219; 564/411
[58] Field of Search ................ 564/146, 166, 411, 219

[56] References Cited

U.S. PATENT DOCUMENTS

| | | | |
|---|---|---|---|
| 1,920,828 | 8/1933 | Wyler | 564/146 X |
| 1,963,597 | 6/1934 | Tinker et al. | 260/124 |
| 1,963,598 | 6/1934 | Tinker et al. | 260/124 |
| 2,128,511 | 8/1938 | Biswell et al. | 260/578 |
| 3,894,078 | 7/1975 | Fridinger | 260/501.19 |
| 4,013,444 | 3/1977 | Fridinger . | |
| 4,139,558 | 2/1979 | Stopp et al. | 260/562 |

OTHER PUBLICATIONS

Roberts et al., "Basic Principles of Organic Chemistry", pp. 801–809 and 862–867 (1964).

*Primary Examiner*—Robert V. Hines
*Attorney, Agent, or Firm*—Gene Harsh; Joseph C. Gil

[57] ABSTRACT

The present invention is directed to a process for preparing 5-nitro-acet-2,4-xylidine comprising:

(a) dissolving acet-2,4-xylidine in an aqueous sulfuric acid solution, said aqueous solution containing from 86 to 92% by weight of sulfuric acid, the weight ratio of sulfuric acid to acet-2,4-xylidine being from 3.5:1 to 6.5:1;

(b) nitrating the resultant solution at a temperature of from 0° to 15° C. in a mixed acid containing nitric acid, sulfuric acid, and from 10 to 25% by weight water; and (c) recovering 5-nitro-acet-2,4-xylidine.

8 Claims, No Drawings

PROCESS FOR THE PRODUCTION OF 5-NITRO-ACET-2,4-XYLIDINE

BACKGROUND OF THE INVENTION

The present invention relates to an improved process for the production of 5-nitro-acet-2,4-xylidine. It is the object of this invention to provide a process for the manufacture of 5-nitro-acet-2,4-xylidine whereby the same is obtained in good yield. Another object is to provide a process in which an acceptably low amount of 6-nitro-acet-2,4-xylidine is produced. Another object is to provide a process in which relatively large batch sizes can be made and in which significant amounts of sulfonation side-reaction can be avoided.

The compound, 5-amino-acet-2,4-xylidine, is known in the art and is used as an intermediate for the preparation of 5-acetamido-2,4-dimethyl-trifluoro-methane-sulfonanilide (see, e.g., U.S. Pat. Nos. 3,894,078 and 4,013,444). In general, 5-amino-acet-2,4-xylidine can be produced by catalytically hydrogenating 5-nitro-acet-2,4-xylidine. The 5-nitro-acet-2,4-xylidine is generally produced by first dissolving acet-2,4-xylidine in a concentrated aqueous sulfuric acid solution (i.e., 96% sulfuric acid) and thereafter nitrating with a mixed solid. The 5-nitro-acet-2,4-xylidine is then recovered. In general, the 5-nitro isomer is not recovered in pure form but also in mixture with the 3-nitro and 6-nitro isomers. The presence of 6-isomer ultimately can lead to difficulties of purification of 5-acetamino-2,4-dimethyl-trifluoromethylsulfonanilide and therefore is undesirable.

The above procedure, making use of 96% sulfuric acid, cannot be used for relatively large batch sizes due to the acceptable amounts of sulfonation side-reaction of acet-2,4-acetxylidine which takes place due primarily to the long charging times. Thus, for example, at least 15% by weight of acet-2,4-xylidine undergoes sulfonation reaction in 97.5% sulfuric acid at 25° C. in only 1 hour, and around 5% undergoes sulfonation in 95% sulfuric acid in only 5 hours. The use of dilute sulfuric acid as reaction medium effectively diminishes the rate of sulfonation; thus, for example, only around 0.5% acet-2,4-xylidine undergoes sulfonation in 90% sulfuric acid in as many as 29 hours.

However, according to the prior art, the concentration of sulfuric acid as solvent has a dramatic effect on the regioselectivity of the nitration reaction of aromatic acetylamino-compounds. Compare for example, U.S. Pat. No. 4,139,558 and U.S. Pat. Nos. 1,963,598, 1,963,597 and 2,128,511 in which a nitration reaction in 96% sulfuric acid leads to substitution meta to the acetylamino group, while a nitration reaction in 80% sulfuric acid leads to substitution ortho to the acetylamino-group. Therefore, based on the prior art, and based on the fact that nitration of acet-2,4-xylidine in nitric acid alone gave substitution ortho to the acetylamino group affording 6-nitroacet-2,4-xylidine, it would have been expected that nitration in 90% sulfuric acid would have given at least large proportions of product of substitution ortho to the acetylamino group.

Contrary to the expected results, the present invention is based on the surprising discovery that nitration of acet-2,4-xylidine in 90% sulfuric acid affords about 96% specific substitution meta to the acetylamino group. The remarkable meta selectivity in nitrating acet-2,4-xylidine in 90% sulfuric acid cannot be attributed to the directing influence of the methyl groups since the opposite selectivity is observed by nitrating in aqueous nitric acid (sp. gr. 1.42) yielding only 6-nitro-acet-2,4-xylidine. The greater influence of the acetylamino group than the methyl group in determining the position of substitution is also illustrated by the example of U.S. Pat. No. 2,128,511 in which N-acetyl-4-toluidine is nitrated in a relatively high sulfuric acid concentration, say about 80%, in which the substitution is predominantly ortho to the acetylamino group affording N-acetyl-3-nitro-toluidine. Thus the use of 90% sulfuric acid as reaction solvent allows a process of a relatively large batch size in which significant amounts of sulfonation side-reaction can be avoided, allows a process in which relatively small amounts of undesirable 6-nitro-acet-2,4-xylidine are formed, and allows a process in which 5-nitro-acet-2,4-xylidine is obtained in good yield.

DESCRIPTION OF THE INVENTION

The present invention is thus directed to a process for preparing 5-nitro-acet-2,4-xylidine comprising:

(a) dissolving acet-2,4-xylidine in an aqueous sulfuric acid solution, said aqueous solution containing from 86 to 92% by weight of sulfuric acid, the weight ratio of sulfuric acid to acet-2,4-xylidine being from 3.5:1 to 6.5:1;

(b) nitrating the resultant solution at a temperature of from 0° to 15° C. in a mixed acid containing nitric acid, sulfuric acid, and from 10 to 25% by weight water; and (c) recovering 5-nitro-acet-2,4-xylidine. In the first step of the process of the present invention, acet-2,4-xylidine is dissolved in an aqueous sulfuric acid solution. In general, the first step is conducted at a temperature of from 0° to 20° C. and preferably at a temperature of from 5° to 20° C. The aqueous sulfuric acid solution used in the first step of the process generally contains from 86 to 92% and preferably 86 to 90% by weight of sulfuric acid. The aqueous sulfuric acid solution is used in an amount such that the weight ratio of sulfuric acid to acet-2,4-xylidine is from 3.5:1 to 6.5:1 and preferably from about 4:1 to about 6:1.

The resultant solution is then nitrated in a known manner, generally at a temperature of from 0° to 15° C. and preferably from 0° to 10° C., using a mixture of nitric acid, sulfuric acid and preferably water (hereinafter referred to as "mixed acid"). The mixed acid useful herein preferably contains from 10 to 25%, more preferably 15 to 20%, and most preferably about 20% by weight of water. The mixed acid is added in such an amount that the molar ratio of nitric acid to acet-2,4-xylidine is from 0.9:1 to 1.05:1, preferably from 0.95:1 to 1.01:1, and most preferably about 0.99:1.

Following nitration, the 5-nitro-acet-2,4-xylidine is recovered. The product may be recovered by introducing the reaction mixture into water maintained at a temperature of from 0° to 50° C. In general, following introduction of the reaction mixture into water, the temperature is allowed to rise (however, the temperature should not be permitted to rise higher than 50° C.). The temperature may be maintained by the addition of ice or by using cooling coils. The reaction product which precipitates out of the solution can then be filtered off, preferably using a filter press.

Alternatively, the reaction product may be recovered utilizing the process described in U.S. application Ser. No. 278,545, filed June 29, 1981 and now U.S. Pat. No. 4,341,802. In this process, the reaction mixture is introduced into an aqueous sulfuric acid solution containing from 25 to 45%, and preferably from 30 to 40%, by weight of sulfuric acid. The temperature is then maintained at from 20° to 50° C., and preferably at from 30° to 40° C. In a particularly preferred embodiment, the reaction mixture is introduced into a 34% sulfuric acid solution and maintained at a temperature of 30° to 40° C. by introducing ice into the mixture and by controlling the cooling. Addition of seeding crystals of 5-nitro-acet-2,4-xylidine to the dilute sulfuric acid can assist the crystallization of the desired 5-nitro isomer. After all the reaction mixture has been introduced, the resultant slurry will have a sulfuric acid concentration (based only on water and sulfuric acid) of from 30 to 50%, preferably from 40 to 48%, and most preferably from about 43 to 45% by weight. The temperature may be maintained by the addition of ice or by using cooling coils. The reaction product which precipitates out of the solution can then be filtered off at 25° to 45° C., preferably at 35° to 40° C, preferably using a filter press.

It has also been found that the total amount of sulfuric acid in the slurry should be controlled relative to the amount of nitro isomers in order to achieve both high purity and good yields. When the sulfuric acid concentration in the slurry is from 30 to 50% by weight, the molar ratio of sulfuric acid to nitro isomers should be from 53:1 to 10:1. The relationship between the sulfuric acid concentration in the slurry to the molar ratio of sulfuric acid to nitro isomers is such that when the sulfuric acid concentration is 30%, the molar ratio should be 53:1. Similarly if the sulfuric acid concentration is 50%, the molar ratio should be 10:1. When the sulfuric acid concentration is from 40 to 48% by weight, the molar ratio should be from 39:1 to 12:1. Finally, in the most preferred embodiment, when the sulfuric acid concentration is from 43 to 45% by weight, the molar ratio should be from 24:1 to 15:1. The amount of nitro-isomers in the slurry can be readily determined since the acet-2,4-xylidine will react with the nitric acid present during nitration substantially stoichiometrically (i.e., generally to a degree of about 99%).

In general, it may sometimes be necessary to rinse any equipment parts with aqueous sulfuric acid to assure that all material has been added or removed. Thus, for example, aqueous sulfuric acid may be used to rinse the reaction vessel after the reaction mixture has been introduced into the water or the aqueous sulfuric acid solution. The resultant rinse is then also introduced in the drowning media.

It should be emphasized that the keys to the present invention reside in the use of an aqueous sulfuric acid solution containing 86 to 92% by weight sulfuric acid to dissolve the acet-2,4-xylidine, and the sulfuric acid to acet-2,4-xylidine weight ratio.

The invention is further illustrated but is not intended to be limited by the following Examples, in which all parts and percentages are by weight unless otherwise specified.

EXAMPLE 1

About 50 parts of acet-2,4-xylidine were dissolved in about 323 parts of an aqueous sulfuric acid solution (86.6% by weight sulfuric acid) and were then nitrated with 78.5 parts of a mixed acid consisting of 33% by weight nitric acid, 48% by weight sulfuric acid and 19% by weight water at a temperature maintained at 0° C. for a period of 3 hours. The reaction mixture was then introduced over a total period of about 20 minutes into an open vessel containing 344 parts of water. The temperature was allowed to rise from 25° C. to 40° C. and was maintained at 40° C. during the remainder of the introduction period (about 15 minutes) by the addition of 22 parts of ice. The resultant slurry was cooled from 40° C. to 22° C. with external cooling over about 30 minutes. The precipitate was then filtered off. The yield based on the total amount of 5-nitro, 3-nitro and 6-nitro isomers was 96% of theory.

EXAMPLE 2

About 49 parts of acet-2,4-xylidine were dissolved in about 215 parts of an aqueous sulfuric acid solution (86.6% by weight sulfuric acid) and were then nitrated with about 50 parts of the same mixed acid as used in Example 1 at a temperature of from 2° to 5° C. for a period of 7 hours. The reaction mixture was then introduced over a total period of about 20 minutes into an open vessel containing 489 parts of ice. The temperature was allowed to rise to 15° C. and was kept at 15° C. during the remainder of the introduction period (about 15 minutes) by addition of 22 parts of ice. The resultant slurry was allowed to warm from 15° C. to 22° C. over about 16 hours. The precipitate was then filtered. The yield based on the total amount of 5-nitro, 3-nitro and 6-nitro isomers was 97.4% of theory.

EXAMPLE 3

500 parts of acet-2,4-xylidine were dissolved in 2630 parts of an aqueous sulfuric acid solution (89.9% by weight sulfuric acid) and were then nitrated with 594 parts of the mixed acid used in Example 1 at a temperature of from 4° to 12° C. for a period of 2 hours. 25 parts of a 98% by weight aqueous sulfuric acid solution was used to rinse the vessel which originally contained the mixed acid with the resultant rinse subsequently added to the reaction mixture.

The reaction mixture was then split into two approximately equal portions. The first portion was introduced over a period of about 75 minutes into an open vessel containing 2162 parts of water. The temperature was allowed to rise from 30° C. to 40° C. and was kept at 40° C. during the remainder of the introduction period (about 25 minutes) by addition of 190 parts of ice. The resultant slurry was cooled to 23° over 20 minutes by the addition of 725 parts of ice. The precipitate was filtered. The yield based on the total amount of 5-nitro, 3-nitro and 6-nitro isomers was 94.8% of theory. The product consisted of 89% 5-isomer, 8% 3-isomer and 3% 6-isomer.

The second portion was introduced over a period of 1 hour into an open vessel containing 1843 parts of water. The temperature was allowed to rise from 29° C. gradually to 40° C. and was kept at that temperature during the remainder of the introduction period (about 15 minutes) by external cooling. The resultant slurry was cooled to 23° C. over about 30 minutes by external cooling. The precipitate was filtered. The yield based on the total amount of 5-nitro, 3-nitro and 6-nitro isomer was 93.3% of theory. The product consisted of 88% 5-isomer, 8% 3-isomer, and 4% 6-isomer.

Following introduction of the reactive mixture into the water, in both instances, the initial reaction vessel was rinsed with 20 parts of a 98% by weight aqueous sulfuric acid solution, with the resultant rinse also introduced into the water.

EXAMPLE 4

300 parts of acet-2,4-xylidine were dissolved in 1377 parts of an aqueous sulfuric acid solution (90.3% by weight sulfuric acid) and were then nitrated with 340 parts of the mixed acid used in Example 1 at a temperature of from 3° C. to 8° C. for a period of 2 hours. 9 parts of a 98% by weight aqueous sulfuric acid solution were used in rinse the vessel which originally contained the mixed acid with the resultant rinse subsequently added to the reaction mixture.

The reaction mixture was then split into three portions.

The first portion, 728 parts, was introduced over 15 minutes into an open vessel containing 585 parts water. The temperature was allowed to rise from 30° C. to 50° C. and then was maintained at 50° C. during the remainder of the introduction period (about 10 minutes) by the addition of 100 parts of ice. The resultant slurry was cooled from 50° C. to 20° C. by the addition of 600 parts of ice over about 15 minutes. The precipitate was then filtered. The yield based on the total amount of 5-nitro, 3-nitro, and 6-nitro isomers was 90.6% of theory. The product consisted of about 85% 5-isomer, about 10% 3-isomer, and about 5% 6-isomer.

The second portion, 726 parts, was introduced over 15 minutes into an open vessel containing 585 parts water. The temperature was allowed to rise from 30° C. to 50° C. and then was maintained at 50° C. during the remainder of the introduction period (about 10 minutes) by external cooling. The resultant slurry was cooled from 50° C. to 20° C. over about 30 minutes by external cooling. The precipitate was filtered. The yield based on the total amount of 5-nitro, 3-nitro, and 6-nitro isomers was 86.4% of theory. The product consisted of about 85% 5-isomer, about 10% 3-isomer, and about 5% 6-isomer.

The third portion, 557 parts, was introduced over about 15 minutes into an open vessel containing 225 parts of ice and 225 parts of water. The temperature was allowed to rise from 0° C. to 43° C. The resultant slurry was cooled to 20° C. over about 30 minutes by external cooling. The precipitate was filtered. The yield based on the total amount of 5-nitro, 3-nitro, and 6-nitro isomers was 87.4% of theory. The product consisted of ca. 85% 5-isomer, ca. 10% 3-isomer, and ca. 5% 6-isomer.

EXAMPLES 5–7

In a manner similar to that of Example 3, the nitrations set forth in TABLE I were carried out using the same mixed acid as in Example 1. The conditions, amounts of material and results were as indicated in TABLE I.

TABLE I

| CONDITION | EXAMPLE 5 | EXAMPLE 6 | EXAMPLE 7 |
|---|---|---|---|
| PBW, ACET-2,4-XYLIDINE | 318. | 500 | 500 |
| PBW, AQUEOUS $H_2SO_4$ | 1379 | 2630 | 2630 |
| % BY WEIGHT $H_2SO_4$ IN AQUEOUS $H_2SO_4$ | 89.8 | 90.0 | 90.0 |
| PBW, MIXED ACID | 359 | 574 | 574 |
| TEMP °C., NITRATION | 9–10° C. | 4–6° C. | 4–7° C. |
| CONTACT TIME, HRS, NITRATION | 1¼ | 29 | 3 |
| DROWNING MEDIA (D.M.) | $H_2O$ | 30% $H_2SO_4$ | 30% $H_2SO_4$ |
| PBW, D.M. | 1900 | 6800 | 6721 |
| TOTAL TIME DROWNING, MINUTES | 45 | 60 | 60 |
| ORIGINAL TEMP °C., D.M. | 31 | 29 | 33 |
| FINAL TEMP °C., D.M. | 50 | 39 | 41 |
| PBW, ICE ADDED TO MAINTAIN FINAL TEMP | NONE | 280 | 623 |
| PBW, AQUEOUS, $H_2SO_4$ ADDED AS RINSES | 112 | 55 | 55 |
| (% BY WEIGHT $H_2SO_4$ IN AQUEOUS $H_2SO_4$) | 90 | 98 | 98 |
| PBW, ICE ADDED TO COOL FOR ISOLATION | 1438 | 313 | 475 |
| TEMP. OF ISOLATION °C. | 20 | 36 | 36 |
| YIELD, % THEORY | 94.8 | 77.4 | 80.3 |
| % 5-NITRO ISOMER | 84 | 95.5 | 95.9 |
| % 3-NITRO ISOMER | 12 | 4 | 4 |
| % 6-NITRO ISOMER | 4 | 0.5 | 0.5 |

What is claimed is:

1. A process for preparing 5-nitro-acet-2,4-xylidine comprising:
   (a) dissolving acet-2,4-xylidine in an aqueous sulfuric acid solution, said aqueous solution containing from 86 to 92% by weight of sulfuric acid, the weight ratio of sulfuric acid to acet-2,4-xylidine being from 3.5:1 to 6.5:1,
   (b) nitrating the resultant solution at a temperature of from 0° to 15° C. in a mixed acid containing nitric acid, sulfuric acid and from 10 to 25% by weight water, and
   (c) recovering 5-nitro-acet-2,4-xylidine.
2. The process of claim 1 wherein said aqueous solution contains from 86 to 90% by weight of sulfuric acid.
3. The process of claim 1 wherein the weight ratio of sulfuric acid to acet-2,4-xylidine is from 4:1 to 6:1.
4. The process of claim 1, wherein said mixed acid contains from 15 to 20% by weight water.
5. The process of claim 1 wherein the molar ratio of nitric acid to acet-2,4-xylidine is from 0.9:1 to 1.05:1.
6. The process of claim 5 wherein said molar ratio is from 0.95:1 to 1.01:1.
7. The process of claim 1 wherein said dissolving step is conducted at from 0° to 20° C.
8. The process of claim 1 wherein said nitrating step is conducted at from 0° to 10° C.

* * * * *